United States Patent [19]

Tice et al.

[11] 4,389,330
[45] Jun. 21, 1983

[54] MICROENCAPSULATION PROCESS

[75] Inventors: Thomas R. Tice, Helena; Danny H. Lewis, Gardendale, both of Ala.

[73] Assignee: Stolle Research and Development Corporation, Cincinnati, Ohio

[21] Appl. No.: 194,127

[22] Filed: Oct. 6, 1980

[51] Int. Cl.³ .................... B01J 13/02; A61K 9/50
[52] U.S. Cl. .................... 427/213.36; 424/32;
424/33; 424/35; 424/38; 424/DIG. 14;
427/213.3; 264/4.1; 264/4.3; 264/4.6
[58] Field of Search ................ 252/316; 424/32, 33

[56] References Cited

U.S. PATENT DOCUMENTS

| | | | |
|---|---|---|---|
| 3,576,758 | 4/1971 | Emrick | 252/316 |
| 3,657,144 | 4/1972 | Yoshida | 252/316 |
| 3,691,090 | 9/1972 | Kitajima et al. | 252/316 |
| 3,773,919 | 11/1973 | Boswell et al. | 424/19 |

FOREIGN PATENT DOCUMENTS

| | | |
|---|---|---|
| 1048696 | 7/1963 | United Kingdom . |
| 1048697 | 7/1963 | United Kingdom . |
| 1394780 | 5/1973 | United Kingdom . |

*Primary Examiner*—Richard D. Lovering
*Attorney, Agent, or Firm*—Oblon, Fisher, Spivak, McClelland & Maier

[57] ABSTRACT

Microcapsules laden with an active agent are prepared by a method comprising: (a) dissolving or dispersing an active agent in a solvent and dissolving a wall forming material in said solvent; (b) dispersing said solvent containing said active agent and wall forming material in a continuous-phase processing medium; (c) evaporating a portion of said solvent from said dispersion of step (b), thereby forming microcapsules containing said active agent in the suspension; and (d) extracting the remainder of the solvent from said microcapsules.

17 Claims, No Drawings

MICROENCAPSULATION PROCESS

BACKGROUND OF THE INVENTION

1. Field of the Invention

The present invention relates to a method of preparing microcapsules. More particularly, the present invention relates to a method of preparing microcapsules containing a biologically active agent.

2. Description of the Prior Art

A variety of methods are known by which any type of compound desired can be encapsulated in the form of microcapsules. In the processes the material to be encapsulated is generally dispersed in a solvent containing a wall forming material. At a single stage of the process, solvent is removed from the microcapsules and thereafter the microcapsule product is obtained. An example of a conventional prior art microencapsulation process is shown in U.S. Pat. No. 3,737,337 wherein a solution of a wall or shell forming polymeric material in a solvent is prepared. The solvent is only partially soluble in water. A solid or core material is dissolved or dispersed in the polymer containing solution and thereafter in a single step, the core material containing solution is dispersed in an aqueous liquid which is immiscible with the organic solvent in order to remove solvent from the microcapsules. Another example of a process in which solvent is removed from microcapsules containing a substance in a single step is shown in U.S. Pat. No. 3,523,906. In this process a material to be encapsulated is emulsified in a solution of a polymeric material in a solvent which is immiscible with water and then the emulsion is emulsified in an aqueous solution containing a hydrophilic colloid. Solvent removal from the microcapsules is then accomplished in a single step by evaporation and the product is obtained. In still another process as shown in U.S. Pat. No. 3,691,090 organic solvent is evaporated from a dispersion of microcapsules in an aqueous medium in a single step, preferably under reduced pressure. Similarly, the disclosure of U.S. Pat. No. 3,891,570 shows a method in which solvent from a dispersion of microcapsules in polyhydric alcohol medium is evaporated from the microcapsules by the application of heat or by bringing the microcapsules under reduced pressure. Another example of a one-step solvent removal process is shown in U.S. Pat. No. 3,960,757.

The problem of the conventional encapsulation techniques is that, especially when they are used to microencapsulate a pharmaceutical agent such as progesterone or norgestimate, the drug loading is a limiting factor. Depending on the physical and chemical properties of the excipient and the agent to be microencapsulated, an attempt to prepare microcapsules with too high of a loading results in incomplete encapsulation, i.e., agent crystals protruding out of the microcapsules or growing in the process medium. A need, therefore, has continued to exist for a technique of preparing microparticles of improved characteristics and of higher quality.

SUMMARY OF THE INVENTION

Accordingly, one object of the present invention is to provide a technique of preparing microcapsules containing an active agent of improved material loading levels and of improved quality.

Briefly, this object and other objects of the present invention as hereinafter will become more readily apparent can be attained by a method of preparing microcapsules containing an active agent by (a) dissolving or dispersing an active agent in a solvent and dissolving a wall forming material in said solvent; (b) dispersing said solvent containing said active agent and wall forming material in a continuous-phase processing medium; (c) evaporating a portion of said solvent from said dispersion of step (b), thereby forming microcapsules containing said active agent in the suspension; and (d) extracting the remainder of the solvent from said microcapsules.

DETAILED DESCRIPTION OF THE PREFERRED EMBODIMENTS

The central feature of the present process of obtaining microcapsules of improved characteristics resides in the fact that during preparation solvent is removed from the microcapsules suspended in a fluid medium in two distinct steps rather than in one process step. The two-step solvent removal technique results in a microcapsule product of improved quality and containing a higher level of active agent. The advantage of the present process over the conventional processes is that the present two-step solvent removal technique results in a microcapsule product of unexpectedly higher active agent loading and of unexpectedly higher quality in contrast to conventional microcapsule products prepared by techniques in which solvent is removed in a single step.

A substance to be incorporated in the microcapsules is dissolved in a solvent. Suitable active agents which can be incorporated in the present microcapsules include agricultural chemicals, perfumes, curing agents, dyes, oxidizing agents and biologically active agents. The amount of active agent dissolved or dispersed in the solvent is especially not critical, although the ratio of active agent to the wall forming material is important insofar as that at too high an amount of active agent to wall forming material, microcapsules will not form. Practically, the amount of active agent combined with wall forming material can range up to as high as about 80 pages by weight active agent to 20 parts by weight wall forming material. There is no limit to the lower ratios at which the active agent can be combined with the wall forming material, except that at very low loadings of active agent in the microcapsules, the microcapsules would not be practically useful. However, it is apparent that the more dilute the solution is, the greater the amount of solvent is present which must be eventually removed to form the microcapsule product containing a given level of active agent. Usually from 5 to 30 wt.% of active agent is dissolved or suspended in the solvent.

The solvent employed for the preparation of the solution containing the active agent can be selected from a variety of common organic solvents including halogenated aliphatic hydrocarbons such as chloroform, methylene chloride, methylchloroform and the like; aromatic hydrocarbon compounds; halogenated aromatic hydrocarbon compounds; cyclic ethers such as tetrahydrofuran and the like; alcohols, water, acetone and the like. The solvent must be a material which will dissolve the wall material, which must be chemically inert with respect to the active agent, which must be immiscible with the continuous-phase processing medium and which should have a boiling point below that of the continuous phase processing medium. The amount of the wall material to be dissolved in the solvent depends upon the solubility of the polymer in the solvent and the resulting viscosity of the polymeric solution. The viscosity is related to the final size of the microcapsules. Mixtures of the above solvents can also be used as an appropriate solvent for the active agent. There is an advantage to using solvents of lower boiling point in that they are easier to be eventually removed by simple evaporative techniques.

To the active agent containing solution is added the wall forming material which surrounds and confines the active agent in the microcapsules. The amount of wall forming material added to the solution is such that microcapsules will readily form when the solution is dispersed in the continuous-phase processing medium. Prior to the dispersal of the solvent in the continuous-phase processing medium, both the active agent and wall material should be in the solvent. Normally, from 5 to 35 wt.% of the wall forming material is dissolved in the solvent.

Suitable wall forming materials include polystyrene, ethylcellulose, cellulose acetate, hydroxy propylmethylcellulose phthalate, cellulose acetate, dibutylaminohydroxypropyl ether, polyvinyl butyral, polyvinyl formal, poly(meth)acrylic acid ester, polyvinylacetal-diethylamino acetate, 2-methyl-5-vinyl pyridine methacrylate-methacrylic acid copolymer, polycarbonate, polyesters, polypropylene, vinylchloride-vinylacetate copolymer, polysaccharides, glycerol distearate, and the like. A preferred group of polymeric wall forming materials includes those which are biodegradable such as aliphatic polyesters including polylactide, polyglycolide, polycaprolactone and copolymers thereof.

Following the preparation of the solvent phase containing the active agent and wall forming material microdroplets of the wall forming material containing the active agent are formed by dispersing the solution-containing the active agent and wall material in a continuous-phase processing medium. The continuous-phase processing medium must be immiscible with and have a boiling point higher than the solvent. While the processing medium in many instances is water, examples of nonaqueous continuous-phase processing media include organic liquids such as xylene or toluene, synthetic oils such as silicone oil, and natural oils such as a vegetable oil including peanut oil. Usually a surfactant (emulsifying agent) is added to the continuous-phase processing medium to prevent the microcapsules from agglomerating and to control the size of the solvent microdroplets in the emulsion. A good surfactant for the example when water is used as the continuous-phase processing medium is poly(vinyl alcohol) (PVA) at a concentration of 1 to 10%. The dispersion can be formed by mechanically agitating the continuous-phase processing medium by a device such as a colloid mill, a homogenizer or the like. An emulsion can also be formed by adding small drops of the active agent-wall forming material solution to the continuous-phase processing medium. In a preferred embodiment of the dispersion step the organic solvent solution is dispersed in an aqueous solution containing polyvinylalcohol. The temperature during the formation of the emulsion is not especially critical but can influence the size and quality of the microcapsules. Moreover, depending on the solvent and continuous-phase processing medium employed, the temperature must not be too low or the solvent and processing medium will solidify or the processing medium will become too viscous for practical purposes, or too high that the processing medium will evaporate, or that the liquid processing medium will not be maintained. Moreover, the temperature of the medium can not be too high that the stability of the particular active agent being incorporated in the microcapsules is adversely affected. Accordingly, the dispersion process can be conducted at any temperature which maintains stable operating conditions.

The dispersion which is formed is a stable emulsion and from this dispersion the organic solvent in the microdroplets in the organic solvent immiscible fluid is partially removed in the first step of the solvent removal process. The solvent can easily be removed by common techniques such as heating, the application of a reduced pressure or a combination of both. The temperature employed to evaporate solvent from the microdroplets is not critical, but should not be that high that it degrades any temperature sensitive material employed in the preparation of a given microcapsule nor should it be so high as to evaporate solvent at such a rapid rate to cause defects in the wall forming material. Generally, from 10 to 90%, preferably 40 to 60% of the solvent is removed in the first solvent removal step.

After the first stage solvent removal step, the dispersed microcapsules in the solvent immiscible fluid medium are isolated from the fluid medium by any convenient means of separation. Thus, for example, the fluid can be decanted from the microcapsules or the microcapsule-fluid suspension can be filtered. Still other, various combinations of separation techniques can be used if desired.

Following the isolation of the mirocapsules from the continuous-phase processing medium, the remainder of the solvent in the microcapsules is removed by extraction. In this second step, the microcapsules can be suspended in the same continuous-phase processing medium used in step one, with or without surfactant, or in another liquid. The extraction medium extracts the solvent from the mirocapsules and yet does not dissolve the microcapsules. During the extraction, the extraction medium with dissolved solvent must be removed and replaced with fresh extraction medium. This is best done on a continual basis, where the rate of extraction medium replenishment is critical. If the rate is too slow, agent crystals will protrude from the microcapsules or grow in the extraction medium. Obviously, the rate of extraction medium replenishment for a given process is a variable which can easily be determined at the time the process is performed and, therefore, no precise limits for the rate must be predetermined. After the remainder of the solvent has been removed from the microcapsules, the microcapsules are dried by exposure to air or by other conventional drying techniques such as vacuum drying, drying over a dessiccant, or the like.

The microcapsule product of the present invention is usually made up of particles of a spherical shape although sometimes the microcapsules may be irregularly shaped. The microcapsules can vary in size, ranging from submicron to millimeter diameters. Preferably, submicron to 250-μm diameters are desirable for pharmaceutical formulations allowing administration of the microcapsules with a standard syringe and needle. The microcapsules find utility in a wide variety of applications depending upon the type of deliverable substance incorporated therein. The present microcapsules are especially useful in the administration of a variety of biologically active agents to human and animal subjects. For instance, the present microcapsules when containing a contraceptive agent can be administered to a subject by injection or by transcervical migration and transport to the internal female reproductive organs for birth control. Suitable contraceptive agents include estrogens such as diethyl stilbestrol, 17-beta-estradiol, estrone, ethinyl estradiol, mestranol, and the like; progestins such as norethindrone, norgestryl, ethynodiol diacetate, lynestrenol, medroxyprogesterone acetate, dimethisterone, megestrol acetate, chlormadinone acetate, norgestimate, norethisterone, ethisterone, melengestrol, norethynodrel and the like; and spermicidal compounds such as nonylphenoxypolyoxyethylene glycol, benzethonium chloride, chlorindanol and the like. Other biologically active agents which can be incorporated in the present microcapsules include gastrointestinal therapeutic agents such as aluminum hydroxide, calcium carbonate, magnesium carbonate, sodium carbonate and the like; non-steroidal antifertility agents; parasympathomimetic agents; psychotherapeutic agents; major tranquilizers such as chloropromazine HCl, clozapine, mesoridazine, metiapine, reserpine, thioridazine and the like; minor tranquilizers such as chlordiazepoxide, diazepam, meprobamate, temazepam and the like; rhinological decongestants; sedative-hypnotics such as codeine, phenobarbital, sodium pentobarbital, sodium secobarbital and the like; other steroids such as testosterone and testosterone propionate; sulfonamides; sympathomimetic agents; vaccines; vitamins and nutrients such as the essential amino acids, essential fats and the like; antimalarials such as 4-aminoquinolines, 8-aminoquinolines, pyrimethamine and the like; anti-migraine agents such as mazindol, phentermine and the like; anti-Parkinson agents such as L-dopa; antispasmodics such as atropine, methscopolamine bromide and the like; antispasmodics and anticholinergic agents such as bile therapy, digestants, enzymes and the like; antitussives such as dextromethorphan, noscapine and the like; bronchodilators; cardiovascular agents such as anti-hypertensive compounds, Rauwolfia alkaloids, coronary vasodilators, nitroglycerin, organic nitrates, pentaerythritotetranitrate and the like; electrolyte replacements such as potassium chloride; ergotalkaloids such as ergotamine with and without caffeine, hydrogenated ergot alkaloids, dihydroergocristine methanesulfate, dihydroergocornine methanesulfonate, dihydroergokroyptine methanesulfate and combinations thereof; alkaloids such as atropine sulfate, Belladonna, hyoscine hydrobromide and the like; analgetics; narcotics such as codeine, dihydrocodienone, meperidine, morphine and the like; non-narcotics such as salicylates, aspirin, acetaminophen, d-propoxyphene and the like; antibiotics such as the cephalosporins, chloranphenical, gentamicin, Kanamycin A, Kanamycin B, the penicillins, ampicillin, streptomycin A, antimycin A, chloropamtheniol, metromidazole, oxytetracycline penicillin G, the tetracyclines, and the like; anti-cancer agents; anti-convulsants such as mephenytoin, phenobarbital, trimethadione; anti-emetics such as thiethylperazine; antihistamines such as chlorophinazine, dimenhydrinate, diphenhydramine, perphenazine, tripelennamine and the like; anti-inflammatory agents such as hormonal agents, hydrocortisone, prednisolone, prednisone, non-hormonal agents, allopurinol, aspirin, indomethacin, phenylbutazone and the like; prostaglandins; cytotoxic drugs such as thiotepa, chlorambucil, cyclophosphamide, melphalan, nitrogen mustard, methotrexate and the like; antigens of such microorganisms as *Neisseria gonorrhea, Mycobacterium tuberculosis,* Herpes virus (humonis, types 1 and 2), *Candida albicans, Candida tropicalis, Trichomonas vaginalis, Haemophilus vaginalis,* Group B *streptococcus ecoli, Microplasma hominis, Hemophilus ducreyi, Granuloma inguinale, Lymphopathia venereum, Treponema pallidum, Brucella abortus. Brucella melitensis, Brucella suis, Brucella canis, Campylobacter fetus, Campylobacter fetus intestinalis, Leptospira pomona, Listeria monocytogenes, Brucella ovis,* Equine herpes virus 1, Equine arteritis virus, IBR-IBP virus, BVD-MB virus, *Chlamydia psittaci, Trichomonas foetus, Toxoplasma gondii, Escherichia coli, Actinobacillus equuli, Salmonella abortus ovis, Salmonella abortus equi, Pseudomonas aeruginosa, Corynebacterium equi, Corynebacterium pyogenes, Actinobaccilus seminis, Mycoplasma bovigenitalium, Aspergillus fumigatus, Absidia ramosa, Trypanosoma equiperdum, Babesia caballi, Clostridium tetani,* and the like; antibodies which counteract the above microorganisms; and enzymes such as ribonuclease, neuramidinase, trypsin, glycogen phosphorylase, sperm lactic dehydrogenase, sperm hyaluronidase, adenossinetriphosphatase, alkaline phosphatase, alkaline phosphatase esterase, amino peptidase, trypsin chymotrypsin, amylase, muramidase, acrosomal proteinase, diesterase, glutamic acid dehydrogenase, succinic acid dehydrogenase, beta-glycophosphatase, lipase, ATP-ase alpha-peptate gamma-glutamylotranspeptidase, sterol-3-beta-ol-dehydrogenase, DPN-di-aprorase.

Having generally described the invention, a further understanding can be obtained by reference to certain specific examples which are provided herein for purpose of illustration only and are not intended to be limiting unless otherwise specified.

EXAMPLE 1

A 2.5 g amount of progesterone and 10 g of poly(DL-lactide) were dissolved in 38 g of methylene chloride. The organic solution was dispersed as microdroplets in 120 g of 5% aqueous poly(vinyl alcohol). The dispersion was obtained by the addition of the organic solution to a stirred aqueous poly(vinyl alcohol) solution contained in a 200-ml resin kettle. A Teflon turbine impeller driven by Fisher Stedi-Speed motor was used to stir the emulsion.

After a stable oil-in water emulsion was prepared, the pressure over the emulsion was continuously reduced and kept just above the point at which foaming occurred. The solvent evaporation step continued until 40 to 60% of the methylene chloride had been removed. The microcapsule suspension was centrifuged at 41 G for 10 minutes. The supernatant was then decanted, the microcapsules were resuspended with 50–100 ml of deionized water, and half of this suspension was poured into fine (4–5.5 μm) fritted-glass funnel. Suction was applied and the microcapsules were slowly filtered. During filtration the microcapsules were kept in suspension by gently stirring them and by continually adding more deionized water. The microcapsules were washed in this manner until about 400 to 500 ml of deionized water were used. This washing step extracted residual methylene chloride remaining in the microcapsules and hardened the microcapsules.

The microcapsules were allowed to settle while the last 10 ml of water was being removed. After the water had drained from the microcapsule cake for about one minute, the cake was quickly broken into smaller pieces with a spatula. While still maintaining suction on the filter funnel, the microcapsules were continually stirred in the funnel for 30 minutes. The microcapsules were then reasonably dry, and were immediately sieved through a 250-μm stainless steel screen using a camel-hair brush. The sieving action aided in drying the microcapsules. After the 250-μm sieving, the microcapsules could be sieved easily through smaller screen sizes or they could be left overnight to dry. The final product consisted of free flowing spherical particles comprising 20% of progesterone (by weight) in poly(DL-lactide).

EXAMPLE 2

A 3 g amount of norgestimate and 3 g of poly(lactide-co-glycolide) were dissolved in 18 g of methylene chloride. The organic solution was dispersed as microdroplets in 58 g of 5 wt% of aqueous poly(vinyl alcohol). The emulsion was obtained by the addition of the organic solution to a stirred aqueous poly(vinyl alcohol) solution contained in a resin kettle. A Teflon turbine impeller driven by a Fisher Steadi-Speed motor was used to stir the emulsion.

After a stable oil-in-water emulsion was prepared, the pressure over the emulsion was continuously reduced and kept just above the point at which foaming occurred. The solvent evaporation step continued until 40 to 60% of the methylene chloride had been removed. The microcapsule suspension was centifuged at 27 G for 3 minutes. The supernatant was then decanted; the microcapsules were resuspended with 50-100 ml of deionized water and were poured into a fine (4-5.5 μm) fritted-glass funnel. Suction was applied and the microcapsules were slowly filtered. During filtration the microcapsules were kept in suspension by gently stirring them and by continually adding more deionized water. The microcapsules were washed in this manner until about 2000 ml of deionized water were used. This washing step extracted residual methylene chloride remaining in the microcapsules and hardened the microcapsules.

The microcapsules were allowed to settle while the last 10 ml of water was being removed. After the water had drained from the microcapsule cake for about one minute, the cake was quickly broken into smaller pieces with a spatula. While still maintaining suction on the filter funnel, the microcapsules were continually stirred in the funnel for 30 minutes. The microcapsules were then reasonably dry, and were immediately sieved through a stainless-steel screen using a camel-hair brush. The final product consisted of free flowing spherical particles comprising 50 wt% of norgestimate in poly(lactide-co-glycolide).

Having now fully described this invention, it will be apparent to one of ordinary skill in the art that many changes and modifications can be made thereto without departing from the spirit or scope of the invention as set forth herein.

What is claimed as new and desired to be secured by Letters Patent of the United States is:

1. A method of preparing microcapsules laden with an active agent, comprising:
   (a) dissolving or dispersing an active agent in a solvent and dissolving a wall forming material in said solvent;
   (b) dispersing said solvent containing said active agent and wall forming material in a continuous-phase processing medium;
   (c) evaporating from 10 to 90 weight % of said solvent from said dispersion of step (b), thereby forming microcapsules containing said active agent in the suspension; and
   (d) extracting the remainder of the solvent from said microcapsules.

2. The method of claim 1, wherein said microcapsules formed in step (c) are separated from said continuous-phase processing medium prior to complete solvent removal in step (d).

3. The method of claim 1, wherein said continuous-phase processing medium is water, xylene, toluene, a synthetic oil or a natural oil.

4. The method of claim 3, wherein said continuous-phase processing medium further comprises a surfactant.

5. The method of claim 4, wherein said continuous-phase processing medium is water containing from 1 to 10% polyvinylalcohol.

6. The method of claim 1, wherein the fluid product of step (b) is a stable water-in-oil or oil-in-water emulsion.

7. The method of claim 1, wherein said solvent is a substance selected from the group consisting of halogenated aliphatic compounds, halogenated aromatic hydrocarbon compounds, aromatic hydrocarbon compounds, cyclic ethers, alcohols, water and acetone.

8. The method of claim 7, wherein said solvent is methylene chloride.

9. The method of claim 1, wherein solvent is evaporated from said dispersion by reducing the pressure over said dispersion.

10. The method of claim 1, wherein residual solvent is removed from said microcapsules in step (d) by washing said microcapsules with water containing a surfactant by vacuum filtration.

11. The method of claim 10, wherein said washed microcapsules are dried by subjecting said microcapsules to a vacuum followed by sieving the microcapsules.

12. The method of claim 1, wherein said wall forming material is polystyrene, ethylcellulose, cellulose acetate, hydroxy propylmethylcellulose phthalate, dibutylaminohydroxypropyl ether, polyvinyl butyral, polyvinyl formal, poly(meth)acrylic acid ester, polyvinylacetaldiethylamino acetate, 2-methyl-5-vinyl-pyridine methacrylate-methacrylic acid copolymer, polycarbonate, a polyester, polypropylene, a vinylchloride-vinylacetate copolymer, a polysaccharide and glycerol distearate.

13. The method of claim 12, wherein said polyester is polylactide, polyglycolide or polycaprolactone or copolymers thereof.

14. The method of claim 1, wherein said active agent is a biologically active agent selected from the group consisting of estrogens, progestins, gastrointestinal therapeutic agents, non-steriodal anti-fertility agents, parasympathomimetic agents, psychotherapeutic agents, major tranquilizers, minor tranquilizers, rhinological decongestants, sedative-hypnotics, non-estrogenic and non-progestational steroids, sulfonamides, sympathomimetic agents, vaccines, vitamins, nutrients, anti-malarial compounds, anti-migraine agents, anti-Parkinson agents, antispasmodics and anticholinergic agents, antitussives, bronchodilators, cardiovascular agents, electrolyte replacements, ergot alkaloids, analgetics, non-narcotics, antibiotics, anti-cancer agents, anti-convulsants, anti-emetics, anti-histamines, anti-inflammatory agents, prostaglandins, cytotoxic drugs, antigens and antibodies and enzymes.

15. The method of claim 1, wherein from 5 to 30 wt% of said active agent is dissolved or dispersed in said solvent.

16. The method of claim 1, wherein from 5 to 35 wt% of said wall forming material is dissolved in said solvent.

17. The method of claim 1, wherein the weight ratio of said active agent to said wall forming material in said solvent ranges up to about 80 wt% active agent to 20 wt% wall forming material.

* * * * *

UNITED STATES PATENT AND TRADEMARK OFFICE
CERTIFICATE OF CORRECTION

PATENT NO. : 4,389,330
DATED : June 21, 1983
INVENTOR(S) : THOMAS R. TICE ET AL

It is certified that error appears in the above-identified patent and that said Letters Patent is hereby corrected as shown below:

In column 2, line 42, delete "pages" and insert therefor--parts--;

In column 3, line 37, delete "solution-con-" and insert therefor--solution con-  --;

In column 4, line 32, delete "mirocapsules" and insert therefor--microcapsules--;

In column 7, line 18, delete "Steadi-Speed" and insert therefor--Stedi-Speed--.

Signed and Sealed this

Eleventh Day of October 1983

[SEAL]

Attest:

GERALD J. MOSSINGHOFF

Attesting Officer        Commissioner of Patents and Trademarks